United States Patent
Schultz et al.

(10) Patent No.: US 9,937,494 B2
(45) Date of Patent: Apr. 10, 2018

(54) REAGENT MIXER AND FLUID CONTROL DEVICES

(71) Applicant: LIFE TECHNOLOGIES CORPORATION, Carlsbad, CA (US)

(72) Inventors: Jonathan Schultz, Guilford, CT (US); Todd Roswech, Guilford, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/739,974

(22) Filed: Jun. 15, 2015

(65) Prior Publication Data

US 2015/0360221 A1 Dec. 17, 2015

Related U.S. Application Data

(60) Provisional application No. 62/012,685, filed on Jun. 16, 2014.

(51) Int. Cl.
| | |
|---|---|
| *B01L 3/00* | (2006.01) |
| *B65D 81/32* | (2006.01) |
| *B01F 15/02* | (2006.01) |
| *G01N 35/10* | (2006.01) |
| *B01F 11/00* | (2006.01) |

(52) U.S. Cl.
CPC .......... *B01L 3/502* (2013.01); *B01F 11/0008* (2013.01); *B01F 11/0065* (2013.01); *B01F 15/028* (2013.01); *B01F 15/0238* (2013.01); *B01L 3/527* (2013.01); *B65D 81/3272* (2013.01); *G01N 35/1002* (2013.01); *B01L 3/505* (2013.01); *B01L 2200/04* (2013.01); *B01L 2200/16* (2013.01); *B01L 2300/022* (2013.01); *B01L 2300/0681* (2013.01); *B01L 2300/0861* (2013.01); *B01L 2300/123* (2013.01); *B01L 2400/0481* (2013.01); *B01L 2400/0487* (2013.01); *Y10T 436/2575* (2015.01)

(58) Field of Classification Search
CPC ...... B01L 3/502; B01L 3/50; Y10T 436/2575; Y10T 436/25; B65D 81/3272; B65D 81/3261; B65D 81/32
USPC ......... 436/180, 174; 422/554, 555, 544, 500
See application file for complete search history.

(56) References Cited

U.S. PATENT DOCUMENTS

| | | |
|---|---|---|
| 2011/0014687 A1 | 1/2011 | Nakamura et al. |
| 2012/0076692 A1 | 3/2012 | Miraghaie |

FOREIGN PATENT DOCUMENTS

| | | |
|---|---|---|
| EP | 0091312 | 10/1983 |
| EP | 2374541 | 10/2011 |

(Continued)

OTHER PUBLICATIONS

International Search Report and Written Opinion of the International Searching Authority for International Application No. PCTUS2015035863 dated Sep. 30, 2015, 14 pages.

(Continued)

*Primary Examiner* — Christine T Mui

(57) ABSTRACT

An apparatus for preparing a reagent solution includes an enclosure and a container disposed within the enclosure. The container defines an internal cavity having a compressible volume and defines a passage providing fluidic communication between the internal cavity and the exterior of the container. Optionally, a compressible member is disposed within the internal cavity. A reagent is disposed within the internal cavity.

17 Claims, 14 Drawing Sheets

(56) References Cited

FOREIGN PATENT DOCUMENTS

| WO | 91/12342 | 8/1991 | | |
| WO | 2012/006185 | 1/2012 | | |
| WO | WO 2012/006185 A1 * | 1/2012 | ............... | B67D 7/60 |
| WO | 2012/151473 | 11/2012 | | |
| WO | WO 2012/151473 A2 * | 11/2012 | .............. | C12M 1/00 |

OTHER PUBLICATIONS

PCT/US2015/035863, International Preliminary Report on Patentabilitiy dated Dec. 20, 2016, 1-10.

* cited by examiner

REAGENT MIXER AND FLUID CONTROL DEVICES

CROSS-REFERENCE TO RELATED APPLICATION(S)

This application claims benefit of U.S. Provisional Application No. 62/012,685, filed Jun. 16, 2014, which is incorporated herein by reference in its entirety.

TECHNICAL FIELD

This application relates to the field of mixing fluids, and in particular, an apparatus and method for preparing a reagent solution.

BACKGROUND

In certain devices, reagents are delivered to produce a reaction product monitored by sensors. However, there are currently no adequate solutions that allow for efficient storage and transportation of reagents that also limit user handling and interaction, including potential contamination, in preparation of the mixed reagents. Thorough and consistent mixing of a reagent in solution is also desirable. In view of the above, it would be advantageous to have a device for preparing a reagent solution which overcame the deficiencies of current approaches.

SUMMARY

In an example, a reagent is disposed in a container including a compressible volume and one or more passages. The pressure of fluid external to the container is increased to drive fluid through the passage and into the container, compressing the compressible volume. When the pressure of the fluid is decreased, the compressible volume decompresses, driving fluid and the reagent out of the container. The container can be disposed in an enclosure, such as a flexible enclosure. One or more of the enclosures including the container can be disposed in a cartridge, which can be pressurized.

BRIEF DESCRIPTION OF THE DRAWINGS

The present disclosure may be better understood, and its numerous features and advantages made apparent to those skilled in the art by referencing the accompanying drawings.

DETAILED DESCRIPTION

Reference will now be made in detail to implementations, examples of which are illustrated in the accompanying drawings. In the following detailed description, numerous specific details are set forth in order to provide a sufficient understanding of the subject matter presented herein. But it will be apparent to one of ordinary skill in the art that the subject matter may be practiced without these specific details. Moreover, the particular implementations described herein are provided by way of example and should not be used to limit the scope of the invention to these particular implementations. In other instances, well-known structures and components have not been described in detail so as not to unnecessarily obscure aspects of the implementations of the invention.

Figure 1:
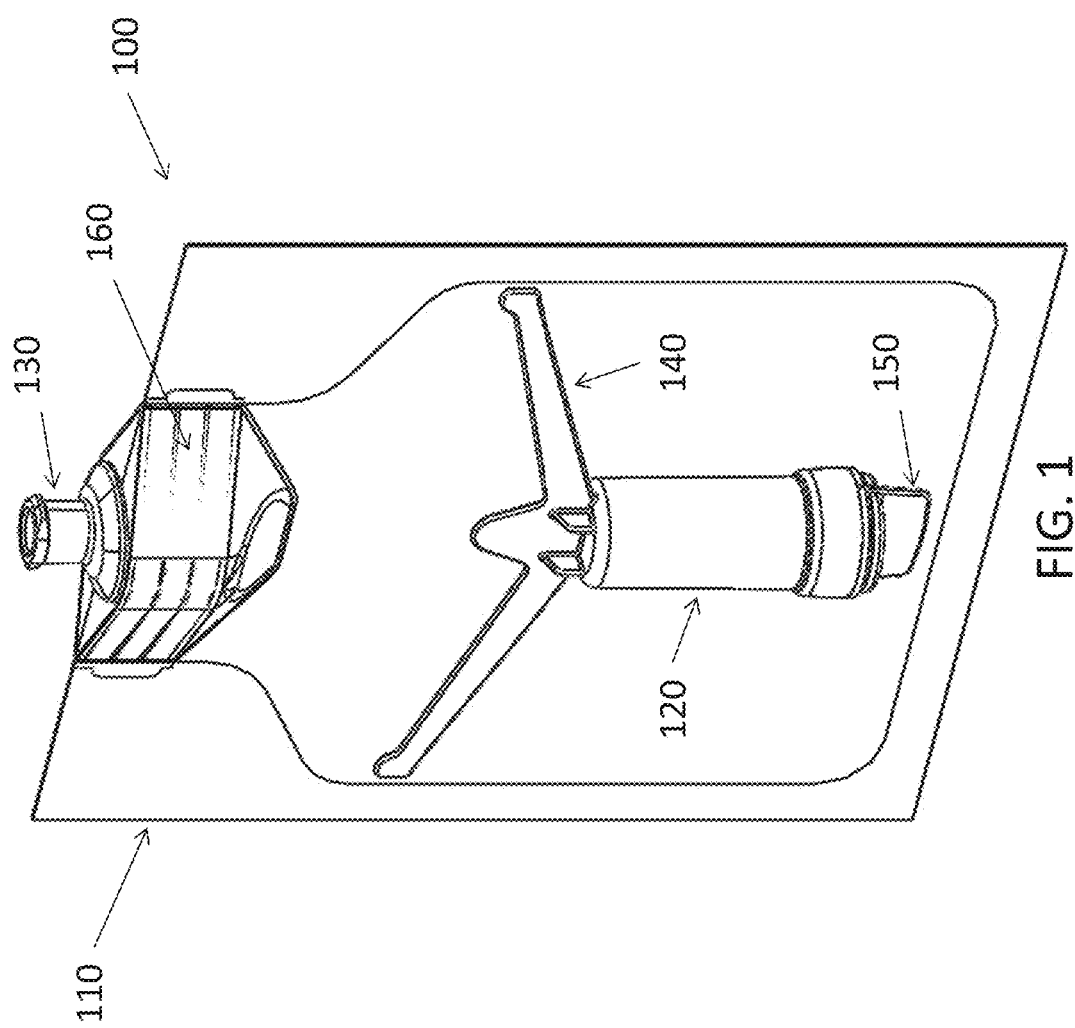
FIG. 1 is a perspective view describing an exemplary reagent storage apparatus.

FIG. 1 is a perspective view describing an exemplary reagent storage apparatus 100. In an example, the reagent storage apparatus 100 can include an enclosure 110. A container 120 is disposed within the enclosure 110. In an example, the enclosure 110 can be a flexible enclosure. A flexible enclosure, such as a sealable flexible bag enclosure, can be pressurized and depressurized by externally applying pressure, such by applying pressurized gas to the external surfaces of the flexible enclosure. Alternatively, the enclosure can be rigid so that externally applied gas pressure does not readily translate to pressure of fluid within the enclosure 110.

The reagent storage apparatus 100 can also include a fluid port 130 coupled to a fitting 160 attached to the enclosure 110 to provide fluid access to the interior of the enclosure 110. The fluid port 130 can be coupled to the fitting 160 to seal the enclosure 110 from an exterior environment after insertion of the container 120. The enclosure 110 can be, for example, thermosealed to itself and the fitting 160, except where otherwise sealed by the fluid port 130.

The container 120 can include one or more arms 140 and a flange 150. The arms 140 can position the container 120 within the enclosure 110, such as approximately centrally, to disperse a reagent within the enclosure 100 evenly. The flange 150 can be provided for convenient assembly of the container 120. In an example, the arm 140 is flexible. For example, the arm 140 can be formed of wire or a polymeric material. Alternatively, the arm 140 can be rigid. Alternatively, the arm 140 and the flange 150 are not limited to those illustrated in FIG. 1 and can include a structure that positions the container within a predetermined location or orientation within the enclosure 110. The container 120 can be directly or indirectly connected to the fluid port 130 or alternatively positioned a suitable distance away from the fluid port 130 as show in FIG. 1. The sealed enclosure 100 including the enclosure 110 and container 120 provides simplified storage and transportation of a reagent within the container 120.

Figure 2:
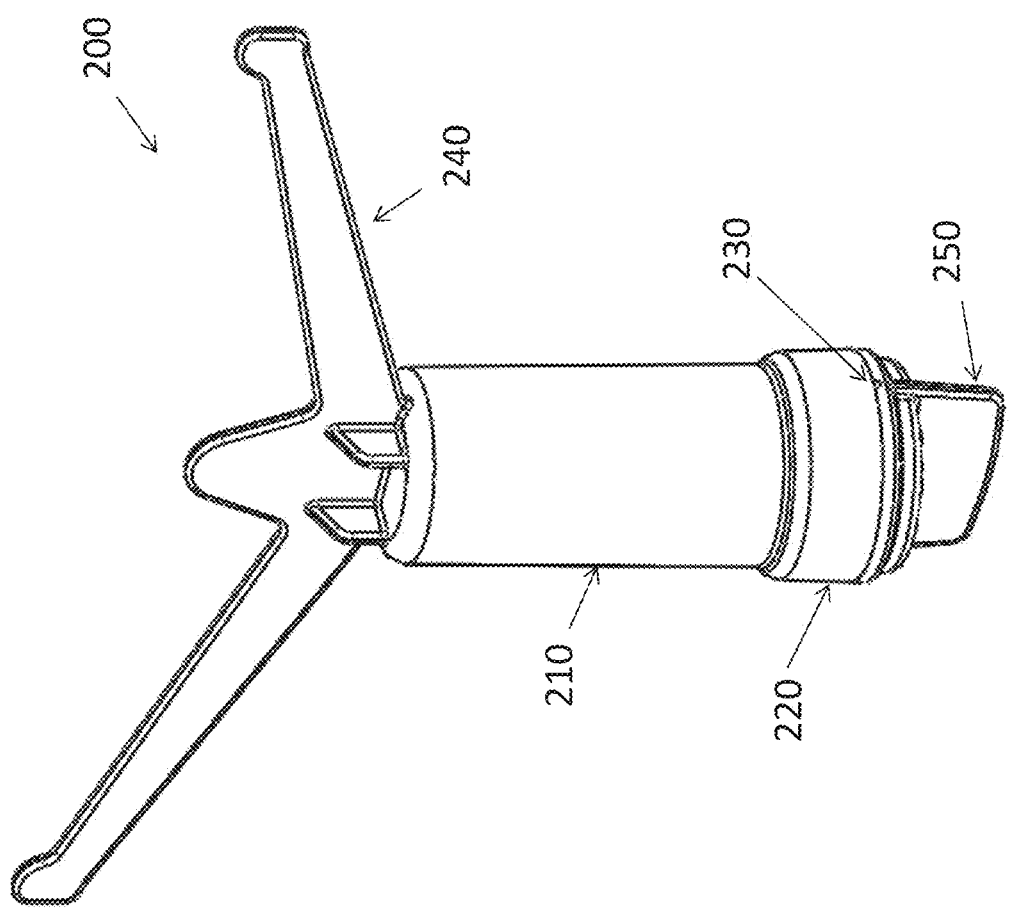
FIG. 2 is a perspective view describing an example container.

FIG. 2 is a perspective view describing an example container 200. The container 200 can include a first portion 210 and a second portion 220 coupled to the first portion 210. Elements such as an optional compressible member and a reagent can be inserted within the container 200 prior to connecting the first portion 210 to the second portion 220. In an example, the second portion 220 can be a cap that slides over or otherwise covers part of the first portion 210 to form the internal cavity. In another example, the second portion 220 can be an insert that slides into the first portion 210. The second portion 220 can be connected to the first portion 210 by any suitable attachment mechanism including screwing the second portion 220 onto the first portion 210 or vice versa, a locking mechanism, adhesive, or any other suitable attachment mechanism.

In an example, the internal cavity defines a compressible volume. The compressible volume compresses in response to fluid pressure and does not dissipate or leave the internal cavity of the container 200. The compressible volume can include a compressible gas volume or can be a compressible member, such as a resilient polymer or foam.

The container 200 can define a passage 230 providing fluidic communication between an internal cavity of the container 200 and an exterior of the container 200. In an example, one or more passages 230 can be defined through to the internal cavity. Such passages 230 can be drilled through the first or second portions of the container 200. In another example, the second portion 220 can include the passage 230 or can include a slot extending beyond a region at which the second portion 220 engages the first portion 210, thus forming the passage 230.

One or more arms 240 can be coupled to the first portion 210 to position the container 200 as desired within an enclosure. A flange 250 can be coupled to the second portion 220 to assist with applying the second portion 220 to the first portion 210 or to position the container 200 away from a bottom of the enclosure.

Figure 3:
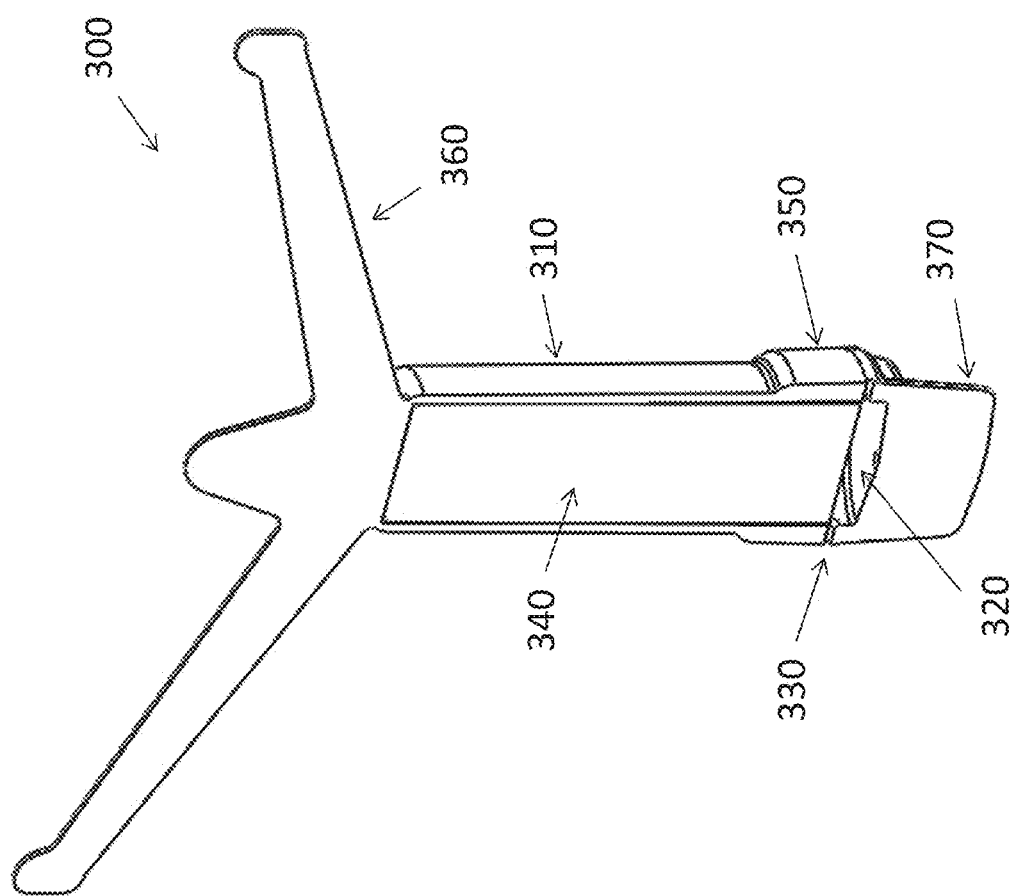
FIG. 3 is a cross-sectional perspective view describing an example container.

FIG. 3 is a cross-sectional perspective view describing an example container 300. The container 300 defines an internal cavity 320 and defines a passage 330 providing fluidic communication between the internal cavity 320 and the exterior of the container 300. The passage 330 can be drilled through the container 300. In another example, a cap or insert can include a slot that extends beyond a region engaging the container 300 and that forms the passage 330. The container 300 can include a first portion 310 and a second portion 350 coupled to the first portion 310 that allows elements such as a compressible member 340 and reagent to be inserted into the internal cavity 320 of the container 300.

The internal cavity 320 defines a compressible volume. The compressible volume is a volume that compresses in response to pressure to match the pressure, and can expand in response to depressuring, providing a counter force on fluid pressure. In an example, the compressible volume includes a compressible gas that compresses to match the pressure of fluid entering the internal volume without dissipating or exiting the internal cavity and in response to a depressurization of the fluid pushes the fluid out of the internal cavity 320. Optionally, the compressible volume can include a compressible member 340. The compressible member 340 is compressible under pressurization and upon depressurization, substantially returns to its previous form. For example, the compressible member 340 can be a foam material. In particular, the compressible member 340 can be a closed-cell foam of elastomeric material. In an example, the compressible member can include polyurethane foam.

In an example, the reagent can be disposed within the second portion 350. The reagent can be a lyophilized nucleotide or an analog thereof. In another example, the reagent is a solution absorbed on a porous metal, ceramic, or polymeric sponge-like material or frit. Optionally, the reagent solution can be frozen. In an alternative example, the reagent can include a pH-adjusting reagent, such as an acid or base.

One or more arms 360 can be coupled to the first portion 310 to position the container 300 as desired within an enclosure. A flange 370 or other suitable appendage can be coupled to the second portion 350 to assist with engaging the second portion 350 with the first portion 310 or to position the container 300 within the enclosure.

Figure 4:
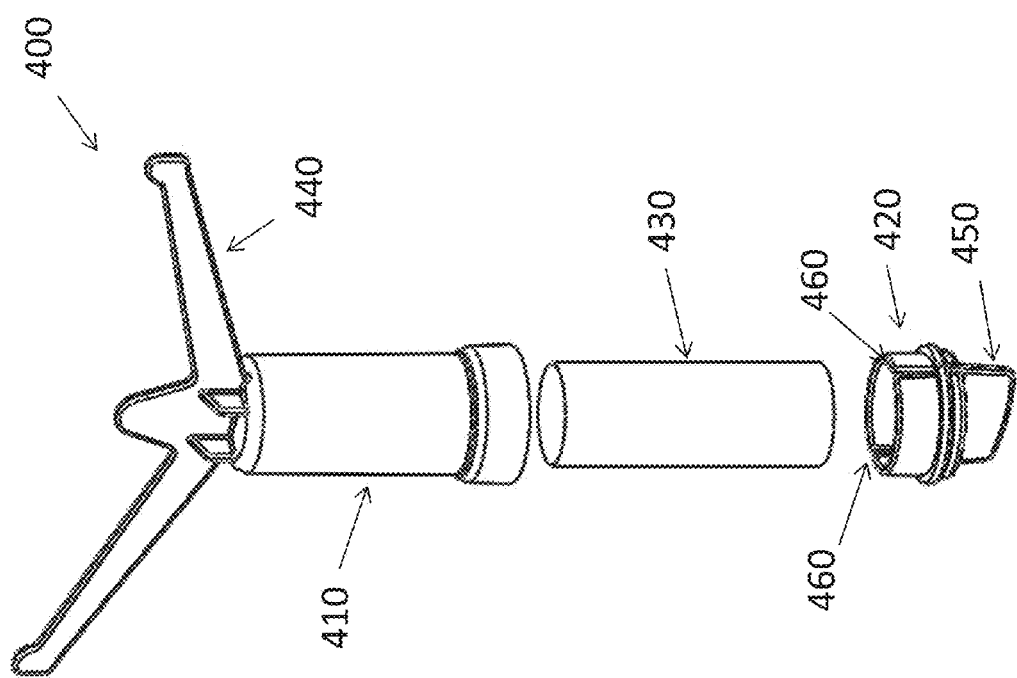
FIG. 4 is an exploded schematic view describing an example container.

FIG. 4 is an exploded schematic view describing an example container 400. The container 400 can include a first portion 410 and a second portion 420 (e.g., an insert) coupled to the first portion 410, allowing elements such as an optional compressible member 430 to be inserted within the container 400. The second portion 420 can be secured to the first portion 410 by sliding or screwing into the first portion 410. One or more flexible arms 440 can be coupled to the first portion 410 to position the container 400 within an enclosure. A flange 450 can be coupled to the second portion 420 to assist with engaging the second portion 420 and the first portion 410 or to position the container 400 within the enclosure.

In an example, the second portion 420 can define one or more slots 460. The first portion 410 and the second portion 420 can engage so as to leave a portion of the one or more slots 460 exposed, providing one or more passages between the internal cavity of the container 400 and the exterior of the container 400.

Figure 5:
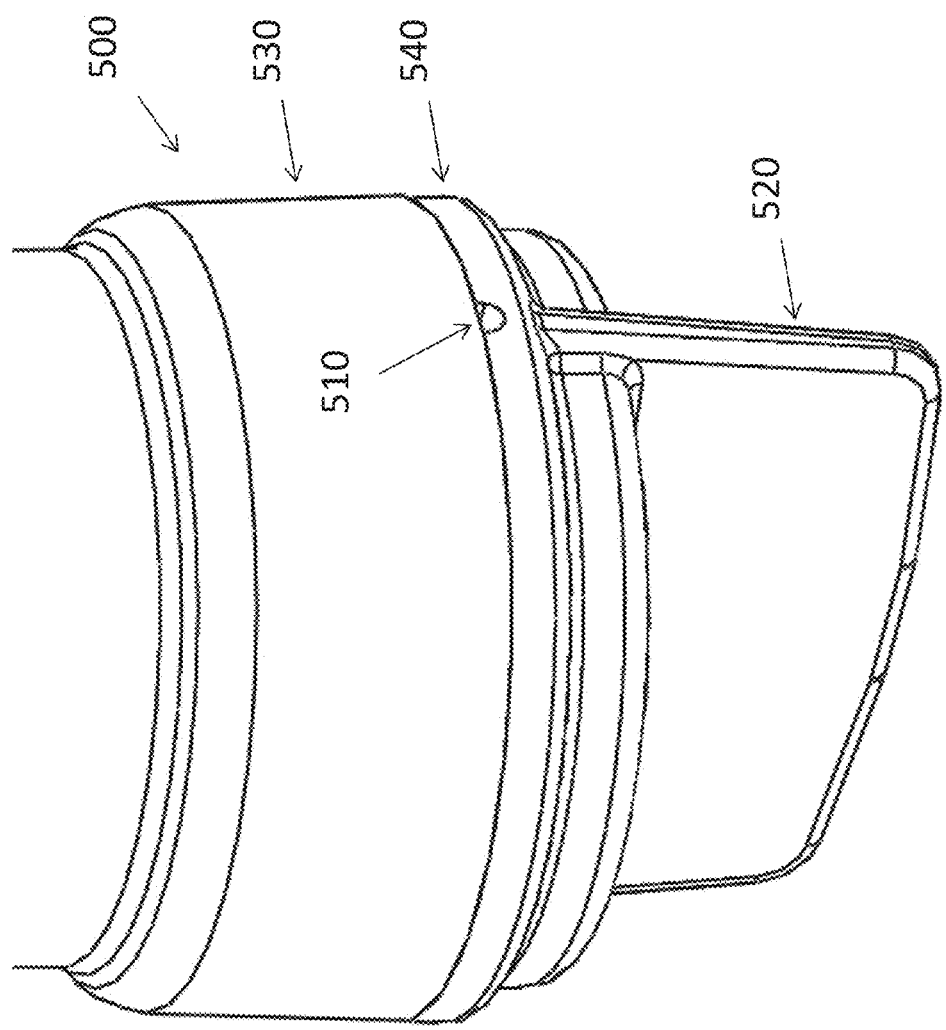
FIG. 5 is a detailed perspective view describing an example container.

FIG. 5 is a detailed perspective view describing an example container 500. The detailed view of the container 500 can define a passage 510 providing fluidic communication between an internal cavity of the container 500 and an exterior of the container 500. An end of the container 500 includes a fitting 530 to receive an insert 540. The insert 540 includes a hole or slot not covered when the insert 540 is applied to the fitting, forming the passage 510. Alternatively, the insert 540 can include a hole, notch, mesh, pores or any other suitable feature for providing fluid communication to the fitting 530. A flange 520 can be coupled to the container 500 to allow control of the insert 540 as it is applied to the fitting 530 and to position the container 200 (as illustrated in FIG. 2) within an enclosure.

Figure 6:
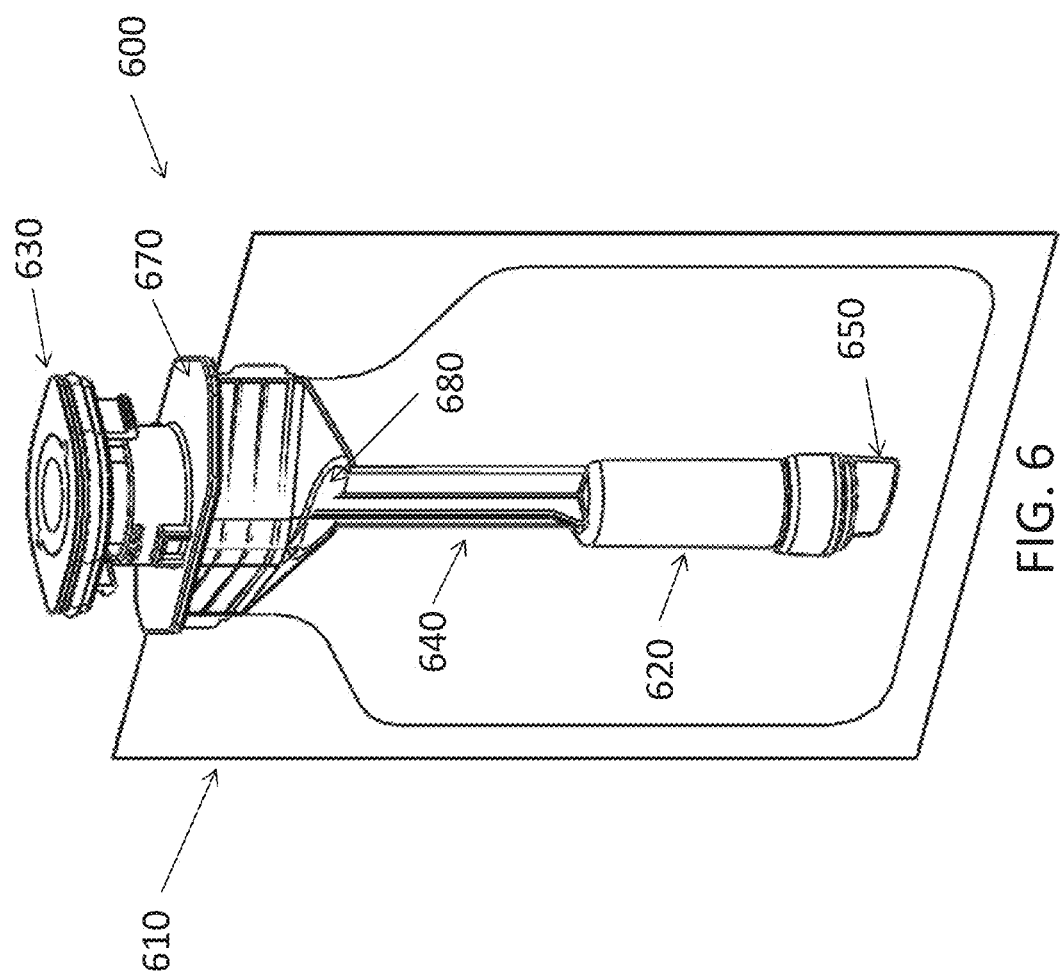
FIG. 6 is a perspective view describing an exemplary reagent storage apparatus.

FIG. 6 is a perspective view describing an exemplary reagent storage apparatus 600. The reagent storage apparatus 600 includes an enclosure 610. A container 620 is disposed within the enclosure 610. The enclosure 610 can be a flexible enclosure as described above. For example, the flexible enclosure can be a sealable flexible bag enclosure that can be pressurized and depressurized externally via fluid pressure or gas pressure. Alternatively, the enclosure 610 can be a rigid enclosure. The enclosure 610 can sealably engage a seal structure 670, such as a fitting, having a bore 680, such as a central bore. The container 620 can be coupled to an arm 640, which can be coupled to a fluid port 630, and inserted through the bore 680 of the fitting 670.

The fluid port 630 provides fluid access to the interior of the enclosure 610 through the bore 680. The fluid port 630 can be coupled to the seal structure or fitting 670 of the reagent storage apparatus 600 from an exterior environment after inserting the container 620. The arm 640 couples the container 620 to the fluid port 630 to position the container 620, for example, approximately centrally within the enclosure 610 to disperse a reagent within the enclosure 610 evenly. The arm 640, the container 620, and the fluid port 630 can be a single integrated piece. In an example fluid flows through the fluid port 630 and through the bore 680 of the fitting 670 into the enclosure 610, optionally along the arm 640. The arm 640 can position the container 620 with or without a flange 650.

Figure 7:
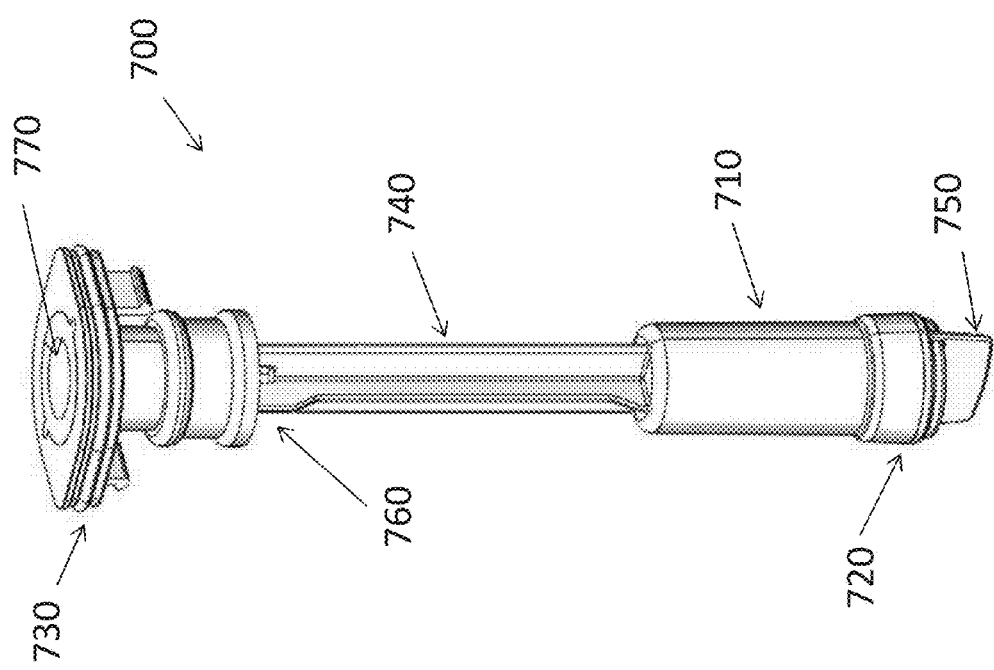
FIG. 7 is a perspective view describing an example container.

FIG. 7 is a perspective view describing an example container 700. The container 700 can include a first portion 710 and a second portion 720 coupled to the first portion 710 allowing elements such as an optional compressible member to be inserted within the container 700. A fluid port 730 is coupled to the container 700 and provides fluid access to an enclosure into which the container 700 is inserted. An arm 740 can coupled the first portion 710 and the fluid port 730 to position the container 700 within an enclosure.

In an example, the second portion 720 is an insert to engage the first portion 710. In another example, the second portion 720 forms a cap to cover an end of the first portion 710. Fluid can flow through the opening 770 of the port 730 and to an opening 760 along the arm 740. The fluid port can include a gasket to facilitate sealing. A flange 750 can be coupled to the second portion 720.

Figure 8:
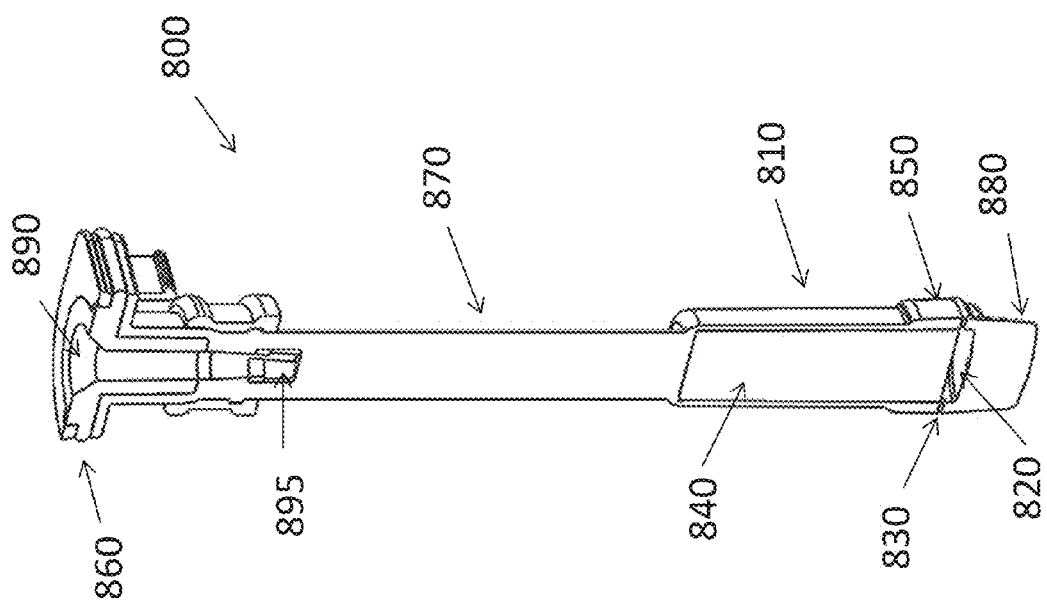
FIG. 8 is a cross-sectional perspective view describing an example container.

FIG. 8 is a cross-sectional perspective view describing an example container 800. The container 800 defines an internal cavity 820 and defines a passage 830 providing fluidic communication between the internal cavity 820 and the exterior of the container 800. The container 800 can include a first portion 810 and a second portion 850 coupled to the first portion 810 defining a compressible volume. In an example, elements, such as a compressible member 840 and reagent, can be inserted into the internal cavity 820 of the container 800.

In an example, the second portion 850 is a cap to apply over an end of the first portion 810. In another example, the second portion 850 is an insert to apply to a fitting of the first portion 810. In an example, a passage 830 is formed in the second portion 850, for example, as a hole or a slot.

The reagent can be disposed within the second portion 850. The reagent can be a lyophilized nucleotide or an analog thereof. In another example, the reagent can be a nucleotide solution absorbed by a porous metallic, ceramic or polymeric sponge or frit. In a further example, the reagent can be frozen. In an additional example, the reagent can include a pH-adjusting reagent, such as an acid or a base.

A fluid port 860 is coupled to the container 800 and provides fluid access to an enclosure in which the container 800 is inserted. For example, fluid entering opening 890 can pass through passages 895 and into an enclosure. An arm 870 can be coupled to the first portion 810 and the fluid port 860. A flange 880 can be coupled to the second portion 850 to also position the container 800 within the enclosure.

The reagent storage apparatus can be inserted into a case or cartridge having a cavity. In an example, pressure can be varied within the cavity to change the pressure of liquid within the flexible enclosure and thus, influence the pressure within the container. Alternatively, pressure can be applied through the opening 890 and internal to the enclosure. In an example, one or more of the enclosures can be incorporated into the case. The case can define one or more pressure chambers in which pressure can be applied and relieved from the enclosures.

Figure 9:
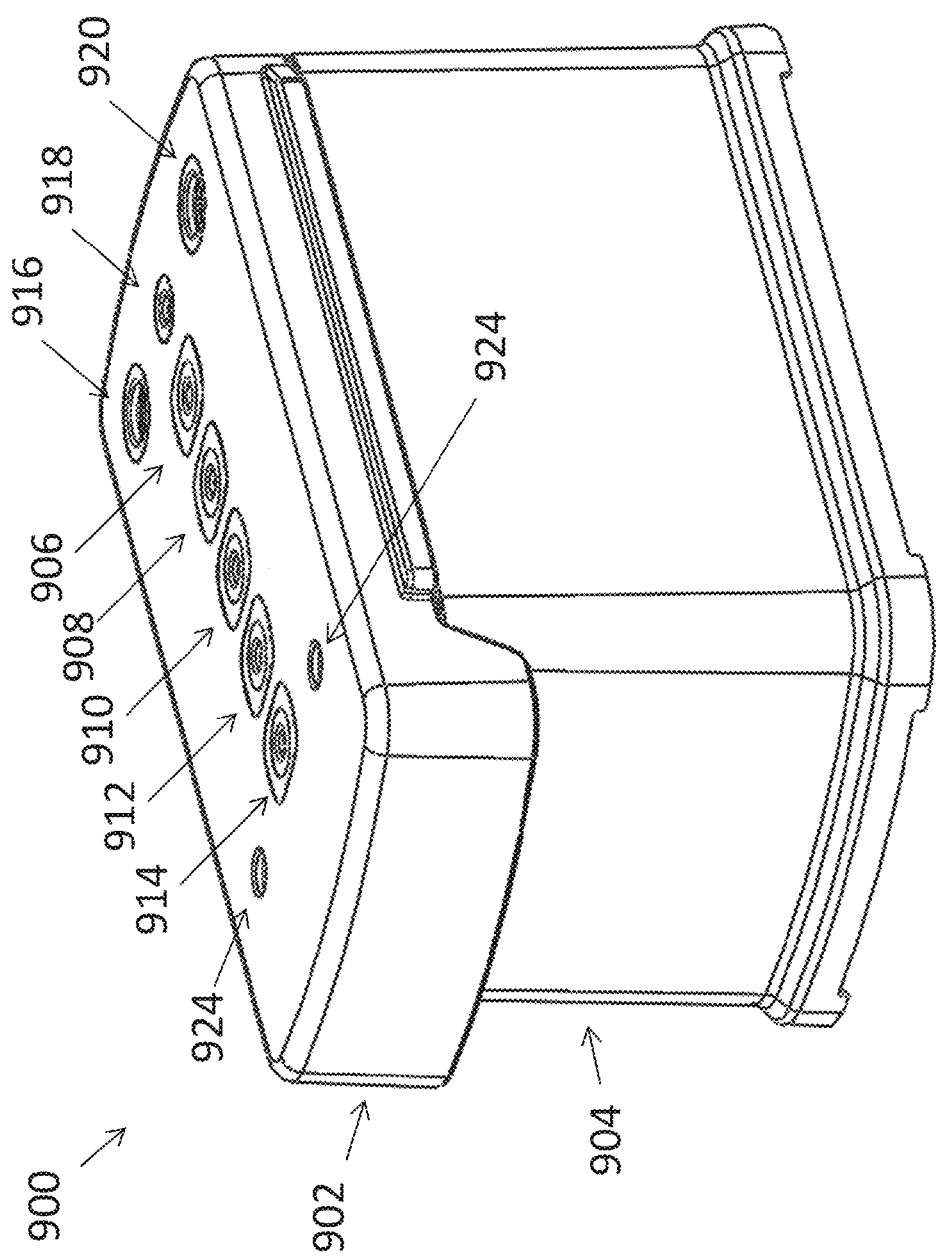
FIG. 9, FIG. 10, FIG. 11, FIG. 12, and FIG. 13 include illustrations of an exemplary cartridge for enclosing one or more enclosures.

In a particular example illustrated in FIG. 9, a cartridge or case 900 includes a lid 902 and a body 904. The lid 902 can receive the fluid ports (906, 908, 910, 912, or 914) of containers inserted into flexible enclosures. The container can include different reagents. For example, each container can include a nucleotide or can include a pH-adjusting reagent. The lid 902 can also include a port 916 for providing pressurized gas or relieving the pressure, controlling the pressure outside of each of the enclosures and thereby controlling pressure within the enclosure. The walls of the base 904 and the lid 902 can be configured to permit pressurizing a cavity within the cartridge 900, for example, with pressurized gas or air. In an example, the cartridge 900 can be labeled with a bar code or radio frequency identification (RFID) tag.

Figure 10:
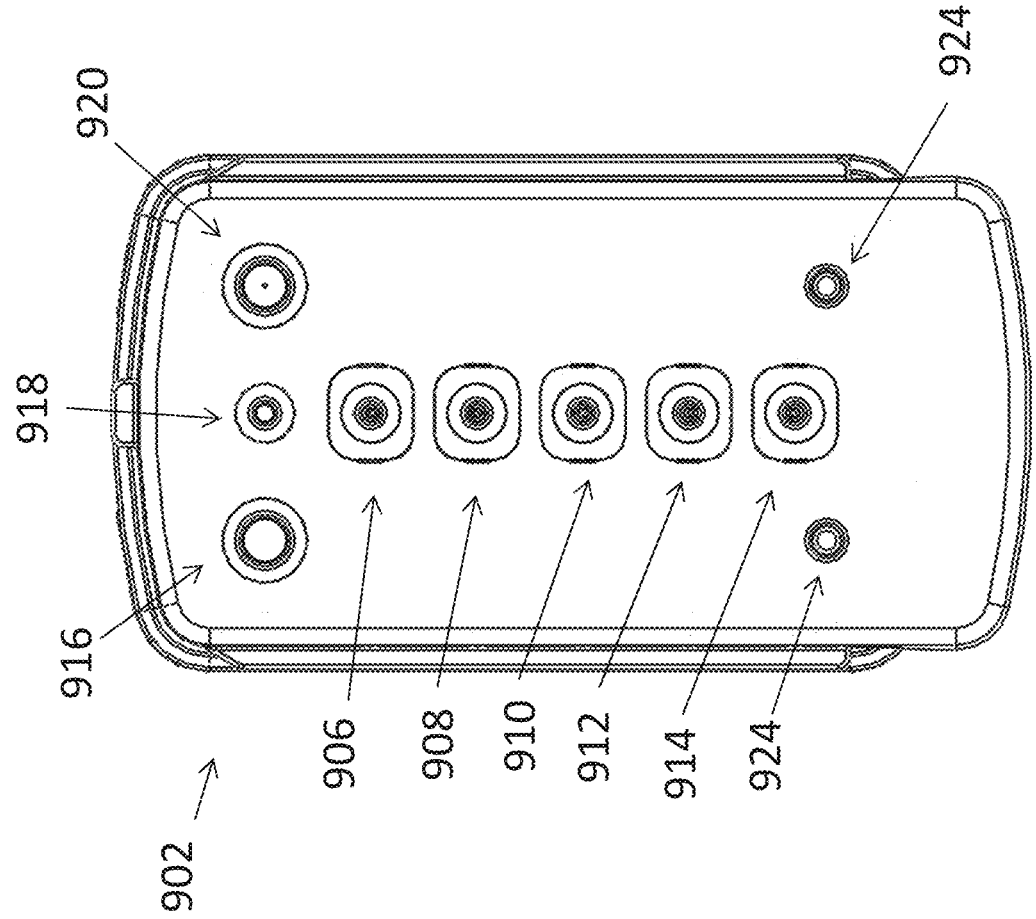

As illustrated in FIG. 9 and FIG. 10, the lid 902 can include access ports 918 and 920 for applying gas or air through a scrubber cartridge. In particular, system can utilize external air, applying the external air through the port 918 and receiving a cleaned gas or air through the port 920. In particular, the scrubber cartridge can include absorbent materials for capturing carbon dioxide or water. Carbon dioxide can be removed from air to prevent acidification of liquid components when carbon dioxide diffuses into the enclosures or when the air is used in other parts of the system.

In a further example, the lid 902 can also include alignment features 924 or 926. Such alignment features can be used to align access to the ports (906, 908, 910, 912, 914, 916, 918, or 920) with a manifold to limit damage to the manifold or provide for adequate engagement between the manifold and the case 900.

Figure 11:
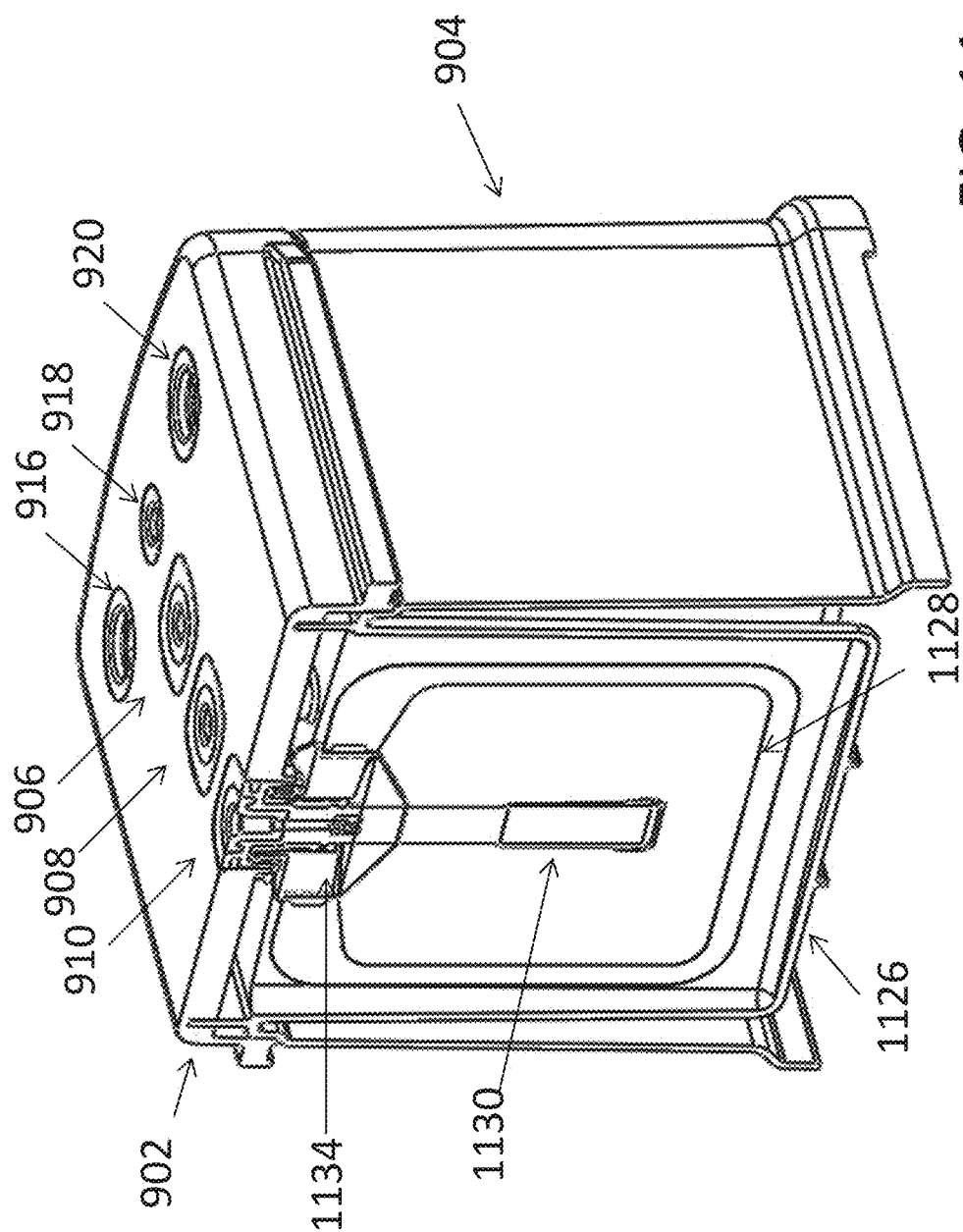
Figure 12:
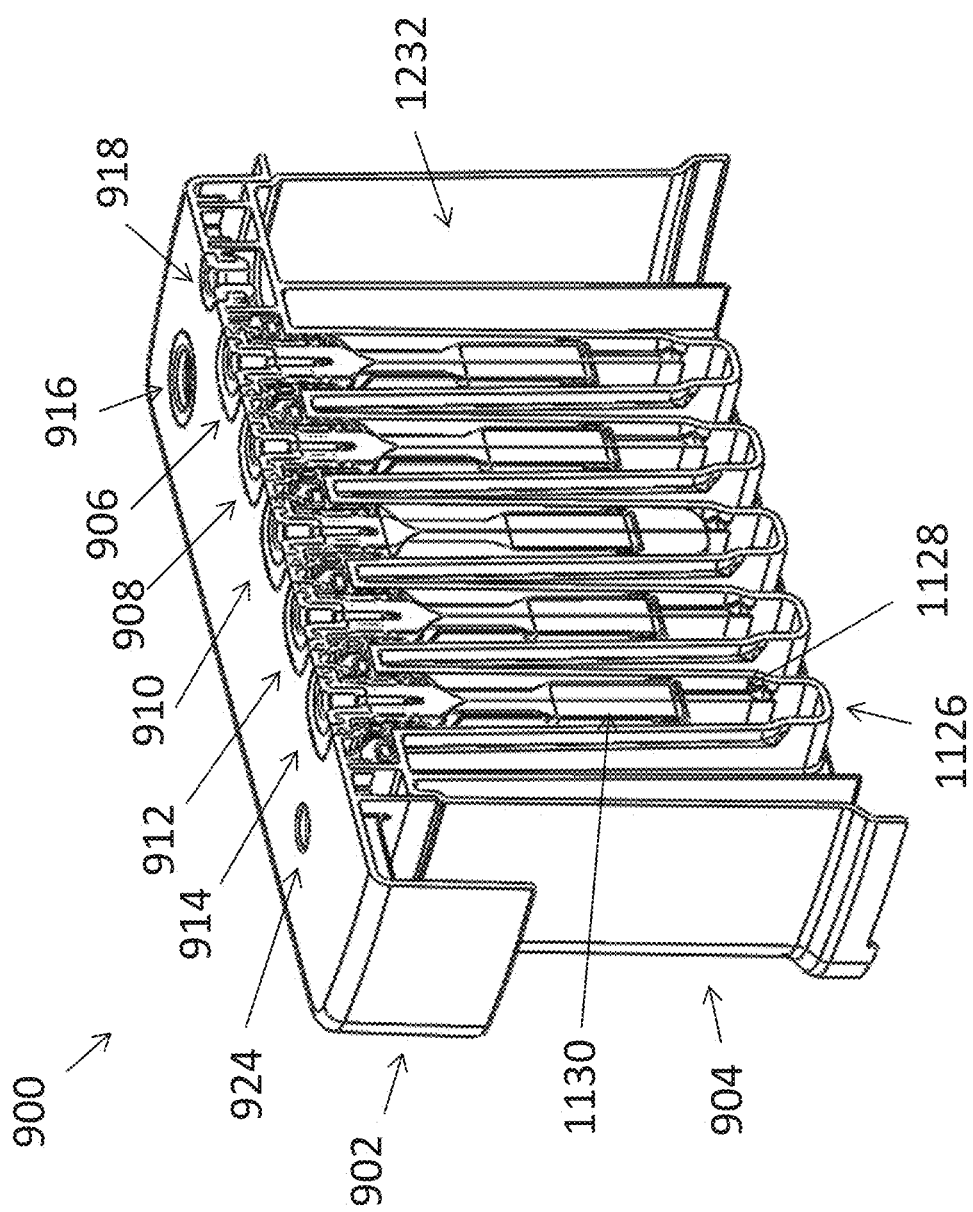
Figure 13:
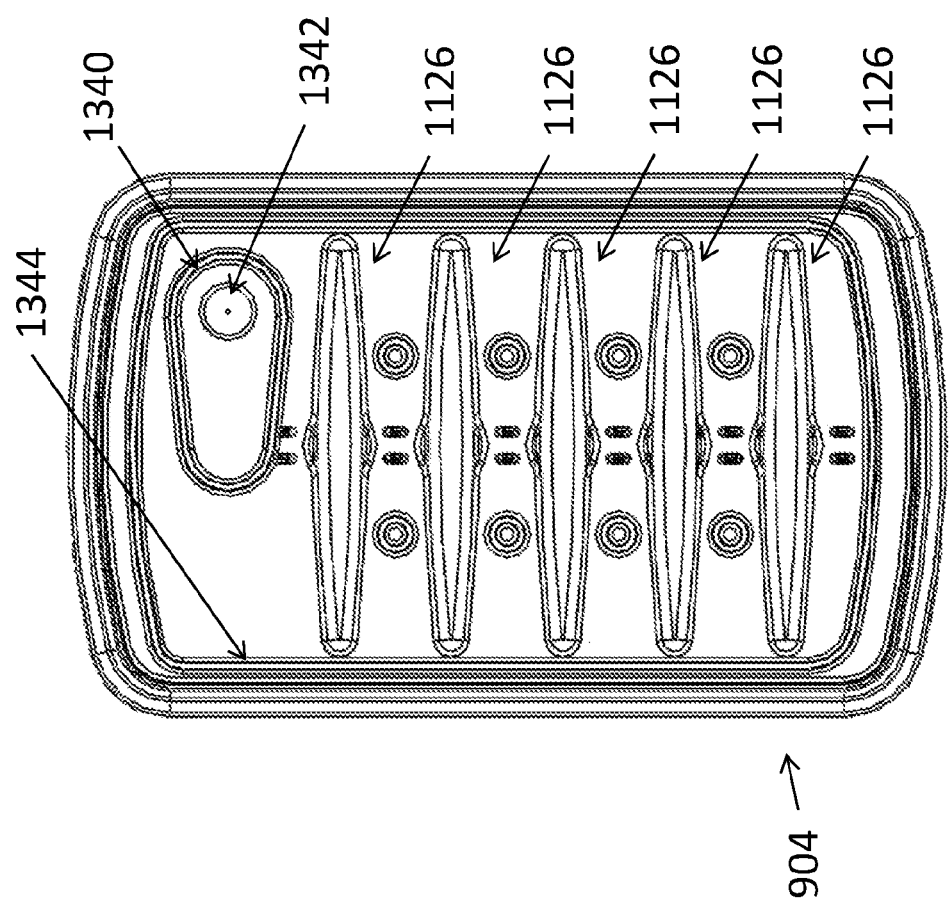

As illustrated in FIG. 11, FIG. 12, and FIG. 13, the body 904 can define individual cavities 1126 into which each enclosure 1128 is placed and the nucleotide container 1130 is inserted. In an example, each enclosure 1128 is disposed within individual cavities 1126 and each container 1130 is applied through the lid 902, engaging the lid 902 at the fluid port of the container 1130. A fitting 1134 of the enclosures 1128 can engage the lid 902.

The lid 902 can define a headspace that provides communication between the pressurized gas input port 916 and each of the cavities 1126. Alternatively, the cavity can be an open cavity absent individualized cavities 1126 and provide a single cavity to which pressurized gas can be applied to apply pressure to the enclosures 1128. As illustrated in FIG. 12, the body 904 can include a chamber 1232 to receive a scrubber cartridge, for example, for removing carbon dioxide from the air.

In a top view, as illustrated in FIG. 13, the body 904 includes individualized cavities 1126. In addition, the body can include a seal structure 1340 to isolate the scrubber cartridge input and output from the pressure of the rest of the body 904. In addition, an internal seal 1342 can be utilized to isolate the input pressure of air entering the scrubber cartridge from the output pressure of air leaving scrubber cartridge. Further, the body 904 can include a seal structure 1344 to engage an opposing seal structure on the lid 902 to provide an isolated interior space including the cavities that can be pressurized or depressurized.

The containers can include nucleotide reagents or other reagents. In particular, individual containers within the cartridge system can include one of four nucleotides. The system can also include a container within an enclosure that includes pH-adjusting reagents. In a particular example, the cartridge includes containers and enclosures incorporating each of the four nucleotides (A, G, C, or T) and optionally, a pH-adjusting reagent container. In an example, the reagents are in dried form. For example, lyophilized nucleotides can be stored within the container. In another example, a reagent solution can be absorbed within a porous metallic, ceramic, or polymeric sponge-like material or frit. In a further example, the reagent solution can be frozen either within a container or within the porous sponge-like material into which the reagent solution is absorbed.

The enclosures described herein can be applied to prepare a reagent solution. Assembly of the enclosure includes inserting a container into the enclosure and sealing the container within the enclosure with a fluid port. One or more enclosures can be further secured into a volume of a case, where the case includes a gas port for providing external gas pressure to the secured enclosures. The enclosures can be inserted into a case as a final assembly step or at a point just prior to mixing that provides flexibility of in the selection of reagents.

Alternatively, the enclosure can be secured to the lid prior to inserting the containers including reagent. The reagent containers can be inserted through the lid and the fluid port of the containers can engage the lid. The lid can be secured to the base following securing the enclosures to the lid or following inserting the containers through the lid into the enclosures.

The pressurization and depressurization of the fluid within the enclosures are controlled by increasing and decreasing the gas pressure of the volume of the case via the gas port.

A method for preparing a reagent solution includes filling an enclosure, such as any of the enclosures described herein including a container and a reagent, with a predetermined amount of fluid through a fluid port of the enclosure. The fluid within the enclosure is then pressurized such that fluid flows into the internal cavity of the container through a passage of the container. The fluid can be pressurized directly through a port. In another example, the fluid can be pressurized by applying external pressure to the enclosure, for example, using gas or other fluidic pressure. The pressurization compresses the compressible volume or member within the internal cavity of the container while the fluid fills a portion of the volume of the internal cavity.

For example, the fluid flows into the internal cavity of the container and compresses the compressible volume or member until the pressure within the internal cavity and exerted on the compressible volume or member is approximately equal to a pressure within the enclosure and external to the container.

After reaching a predetermined pressure, the fluid within the enclosure is depressurized. The compressible volume or member decompresses so as to expand and eject the fluid and reagent from the internal cavity into the enclosure outside of the container. The mixture of reagent and fluid ejected from the passage creates eddy currents and turbulence within the bag enclosure sufficient to mix the reagent with fluid. Upon depressurization, a pressure within the internal cavity as imposed by the compressible volume or member is greater than a pressure within the enclosure and external to the container. The fluid and the reagent eject from the internal cavity through the passage until the pressure within the internal cavity is approximately equal to a pressure within the enclosure and external to the container to provide a well-mixed reagent solution.

Pressurization can be performed by increasing a gas pressure external to a flexible enclosure. In one implementation, the enclosure can be disposed within a case. Pressure within the enclosure can be controlled by increasing/decreasing a gas pressure within the case and external to the enclosure. Proper mixing of the reagent and fluid can be accomplished through repeated cycles of pressurization and depressurization. After mixing is completed, the fluid and the reagent are released through the fluid port of the enclosure.

Exemplary enclosures are useful as reagent reservoirs in biological processes where multiple reagents are delivered to one or more reactors or reaction sites. The reaction sites can be monitored by chemical, electrical or optical sensors. Exemplary systems include methods and apparatuses for carrying out DNA sequencing, and in particular, pH-based DNA sequencing. For example, in pH-based DNA sequencing, base incorporations are determined by measuring hydrogen ions that are generated as natural byproducts of polymerase-catalyzed extension reactions. DNA templates each having a primer and polymerase operably bound are loaded into reaction chambers or microwells, after which repeated cycles of deoxynucleoside triphosphate (dNTP) addition and washing are carried out. Such templates are typically attached as clonal populations to a solid support, such as a microparticle, bead, or the like, and such clonal populations are loaded into reaction chambers. In each addition step of the cycle, the polymerase extends the primer by incorporating added dNTP when the next base in the template is the complement of the added dNTP. If there is one complementary base, there is one incorporation, if two, there are two incorporations, if three, there are three incorporations, and so on. With each such incorporation there is a hydrogen ion released, and collectively a population of templates releasing hydrogen ions causing very slight changes to the local pH of the reaction chamber which is detected by an electronic sensor. In addition to sequencing, the device herein can be useful for other biological instruments that require fluid storage or delivery.

Figure 14:
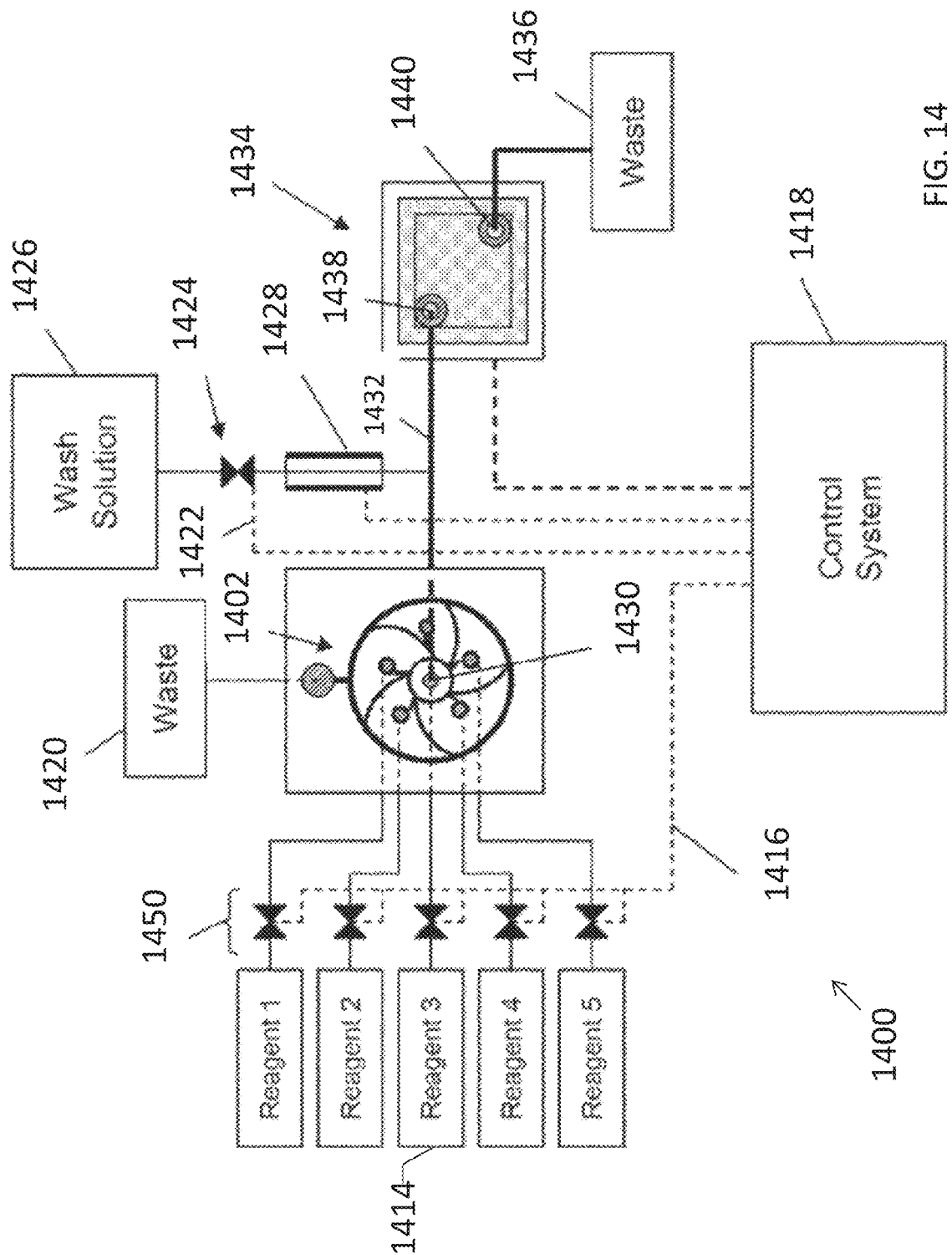
FIG. 14 is a block diagram describing an example system. The use of the same reference symbols in different drawings indicates similar or identical items.

FIG. 14 diagrammatically illustrates a system employing an enclosure 1414 that is a reagent reservoir, for example, for carrying out pH-based nucleic acid sequencing. Each electronic sensor of the apparatus generates an output signal. The fluid circuit permits multiple reagents to be delivered to the reaction chambers.

In FIG. 14, the system 1400 includes a fluidics circuit 1402 connected to at least two reagent reservoirs 1414, to a waste reservoir 1420, and to a biosensor 1434 by fluid pathway 1432 that connects fluidics node 1430 to inlet 1438 of biosensor 1434. The prepared and mixed reagent solution from reservoirs 1414 can be driven to fluidic circuit 1402 by a variety of methods including pressure, pumps, such as syringe pumps, gravity feed, and the like, and are selected by control of valves 1450. Reagents from the fluidics circuit 1402 can be driven to the waste containers 1420 and 1436. The control system 1418 includes controllers for valves 1450 that generate signals for opening and closing via an electrical connection 1416.

The control system 1418 also includes controllers for other components of the system, such as a wash solution valve 1424 connected thereto by the electrical connection 1422, and the reference electrode 1428. The control system 1418 can also include control and data acquisition functions for the biosensor 1434. In one mode of operation, the fluidic circuit 1402 delivers a sequence of selected reagents 1, 2, 3, 4, or 5 to the biosensor 1434 under programmed control of the control system 1418, such that in between selected reagent flows, the fluidics circuit 1402 is primed and washed with a wash solution 1426, and the biosensor 1434 is washed with the wash solution 1426. Fluids entering the biosensor 1434 exit through the outlet 1440 and are deposited in the waste container 1436. A similar setup can be used for optical sequencing systems, with photodiodes or CCD cameras for example.

The enclosure and container components can be constructed from a variety of materials, including metals, glass, ceramics, polymers, or the like. The compressible member can be formed of any inert material such as polyurethane and can be a sponge that is compressible.

As mentioned above, fluidic circuits can be fabricated by a variety of methods and materials. Factors to be considered in selecting materials include degree of chemical inertness required, operating conditions, e.g. temperature, and the like, volume of reagents to be delivered, whether or not a reference voltage is required, manufacturability, and the like. For meso-scale and larger scale fluid deliveries, conventional milling techniques can be used to fabricate parts that can be assembled into fluidic circuits of the invention. In one aspect, plastics such as polycarbonate, polymethyl methacrylate, and the like, can be used to fabricate fluidics circuits of the invention.

The reagent storage devices as described herein can operate as such. Each enclosure can start empty with a container within the enclosure. The container can contain liquid nucleotides or lyophilized nucleotides. The enclosure is deflated by removing any air within the enclosure. This can be done by either suctioning any air out of the bag, by pressurizing the area surrounding the enclosure, or by adding liquid to the enclosure driving any air out. In some instances, during operation, an additional solution can be introduced to the enclosure and the amount introduced can be limited by the walls of the cavity surrounding the enclosure or when pressure in the cavity is equal to or exceeds the pressure of the enclosure during expansion. Any bubbles introduced to the system can be purged from the enclosure. Mixing of the reagents or solutions in the bag can occur by pressurizing and depressurizing the enclosure. Alternatively the solutions can be mixed by vibrating the body in the enclosure. In some embodiments, mixing can occur with pressurization of the contents of the enclosure. For example, external gas pressure can be applied to the bag, causing internal solutions to flow into the container when the compressible volume or member compresses. As the gas pressure is quickly released, the pressure 'charged' within the compressible volume or member forces solution out through passages in the container thereby mixing liquid.

In particular, the above described devices and methods provide technical advantages that address transportation and storage issues for sensitive reagents, such as biomolecules, each, nucleotides. Transportation of such reagents can be accomplished with less concern of contamination, pH change, and degradation.

Methods and devices for mixing a reagent, such as methods and devices for mixing a reagent and fluid within an enclosure, are described. In various implementations, the methods or devices can be combined with a biosensor in fluidic communication with the mixed reagent solution to provide reliable measurement results. The methods or devices are exemplified in a number of implementations, some of which are summarized throughout the specification.

In one aspect, an apparatus includes an enclosure and a container disposed within the enclosure. The container defines an internal cavity and defines a passage providing fluidic communication between the internal cavity and the exterior of the container. A compressible member is disposed within the internal cavity. A reagent is disposed within the internal cavity.

In a related aspect, the enclosure is a flexible bag enclosure. The enclosure includes a fluid port to provide fluid access to the interior of the enclosure.

In a related aspect, an arm is coupled to the container. A set of arms can be coupled to the container to position the container approximately centrally within the enclosure. An arm can be coupled to the container and the fluid port to position the container approximately centrally within the enclosure. The container can include a cap to form the internal cavity. A flange can be coupled to the container and the fluid port to orient the container within the enclosure. The reagent comprises a lyophilized nucleotide or an analog thereof.

In a related aspect, the apparatus further includes a case defining a volume, the enclosure disposed within the volume. The case includes a gas inlet port providing access to the volume and external to the enclosure. The case includes a lid to secure the enclosure and provide fluidic access to a fluid port of the enclosure.

In another aspect, an apparatus includes a case defining a volume and having a gas port. A plurality of enclosures are disposed within the volume and secured to the case. Each enclosure of the plurality of enclosures includes a fluid port providing fluidic access to the interior of the enclosure. A container is disposed within each enclosure. The container defines an internal cavity and defines a passage providing fluidic communication between the internal cavity and the exterior of the container. A compressible member is disposed within the internal cavity. A reagent is disposed within the internal cavity.

In a related aspect, each enclosure of the plurality of enclosures is secured to the container. The container provides fluidic access to the fluid port of the each enclosure. The enclosure can be a flexible bag enclosure. Each enclosure further includes a set of flexible arms coupled to the container to position the container approximately centrally within the enclosure. The reagent of the each enclosure includes a unique lyophilized nucleotide or an analog thereof. The container can include a cap to form the internal cavity. A flange can be coupled to the container and the fluid port to orient the container within the enclosure.

In another aspect, a method for preparing a reagent solution includes filling an enclosure with a fluid through a fluid port of the enclosure. The enclosure includes a container disposed within the enclosure. The container defines an internal cavity and defines a passage providing fluidic communication between the internal cavity and the exterior of the container. A compressible member is disposed within the internal cavity. A reagent is disposed within the internal cavity. The fluid within the enclosure is pressurized, the fluid flowing into the internal cavity of the container and compressing the compressible member. The fluid within the enclosure is depressurized, the compressible member decompressing and ejecting the fluid and reagent from the internal cavity. The reagent mixes with the fluid.

In a related aspect, the enclosure is a flexible enclosure. Pressurizing includes increasing a gas pressure external to the flexible enclosure.

In a related aspect, the enclosure is disposed within a case. Pressurizing includes increasing a gas pressure within the case and external to the enclosure.

In a related aspect, the pressurizing and the depressurizing steps are repeated, and the reagent is further mixed with the fluid. The fluid flows into the internal cavity of the container and compresses the compressible member until the pressure within the internal cavity and exerted on the compressible member is approximately equal to a pressure within the enclosure and external to the container. Upon depressurizing, a pressure within the internal cavity as imposed by the compressible member is greater than a pressure within the enclosure and external to the container. The fluid and the reagent eject from the internal cavity through the passage until the pressure within the internal cavity is approximately equal to a pressure within the enclosure and external to the container. The fluid and the reagent are released through the fluid port.

In another aspect, a method of preparing a reagent solution includes inserting a container into an enclosure. The container defines an internal cavity and defines a passage providing fluidic communication between the internal cavity and the exterior of the container. The container includes a compressible member disposed within the internal cavity and a reagent disposed within the internal cavity. The container is sealed within the enclosure with a fluid port. The enclosure is filled with a fluid through the fluid port. The fluid within the enclosure is pressurized, the fluid flowing into the internal cavity of the container and compressing the compressible member. The fluid within the enclosure is depressurized, the compressible member decompressing and ejecting the fluid and reagent from the internal cavity. The reagent mixes with the fluid.

In a related aspect, the enclosure is a flexible enclosure. Pressurizing includes increasing a gas pressure external to the flexible enclosure.

In a related aspect, the enclosure is disposed within a case. Pressurizing includes increasing a gas pressure within the case and external to the enclosure.

In a related aspect, the pressurizing and the depressurizing steps are repeated, and the reagent is further mixed with the fluid. The fluid flows into the internal cavity of the container and compresses the compressible member until the pressure within the internal cavity and exerted on the compressible member is approximately equal to a pressure within the enclosure and external to the container. Upon depressurizing, a pressure within the internal cavity as imposed by the compressible member is greater than a pressure within the enclosure and external to the container. The fluid and the reagent eject from the internal cavity through the passage until the pressure within the internal cavity is approximately equal to a pressure within the enclosure and external to the container. The fluid and the reagent are released through the fluid port.

In another aspect, a method of preparing a reagent solution includes securing a plurality of enclosures within a volume of a case. The case includes a gas port. Each enclosure includes a container disposed within the enclosure. The container defines an internal cavity and defines a passage providing fluidic communication between the internal cavity and the exterior of the container. The container includes a compressible member disposed within the internal cavity and a reagent disposed within the internal cavity. The enclosure is filled with a fluid through a fluid port of the enclosure. A gas pressure of the volume of the case is increased via the gas port to pressurize the fluid within the enclosure. The fluid flows into the internal cavity of the container and compresses the compressible member. The gas pressure of the volume of the case is decreased via the gas port to depressurize the fluid within the enclosure. The compressible member decompresses and ejects the fluid and reagent from the internal cavity. The reagent mixes with the fluid.

In a related aspect, the enclosure is a flexible enclosure. Pressurizing includes increasing a gas pressure external to the flexible enclosure. The pressurizing and the depressurizing steps are repeated, and the reagent is further mixed with the fluid. The fluid flows into the internal cavity of the container and compresses the compressible member until the pressure within the internal cavity and exerted on the compressible member is approximately equal to a pressure within the enclosure and external to the container. Upon depressurizing, a pressure within the internal cavity as imposed by the compressible member is greater than a pressure within the enclosure and external to the container. The fluid and the reagent eject from the internal cavity through the passage until the pressure within the internal cavity is approximately equal to a pressure within the enclosure and external to the container. The fluid and the reagent are released through the fluid port.

In a first aspect, a method of preparing a reagent solution includes providing a plurality of enclosures within a volume of a cartridge. The cartridge includes a gas port and the enclosure. The enclosure includes a container disposed within the enclosure. The container defines an internal cavity and defines a passage providing fluidic communication between the internal cavity and the exterior of the container. The enclosure also includes a reagent disposed within the internal cavity. The method further includes filling the enclosure with a fluid through a fluid port of the enclosure; increasing a gas pressure of the volume of the cartridge via the gas port to pressurize the fluid within the enclosure, the fluid flowing into the internal cavity of the container and compressing the compressible volume; and decreasing the gas pressure of the volume of the cartridge via the gas port to depressurize the fluid within the enclosure, the compressible volume decompressing and ejecting the fluid and reagent from the internal cavity, the reagent mixing with the fluid.

In an example of the first aspect, the enclosure further includes a compressible member disposed within the internal cavity.

In another example of the first aspect and the above examples, the enclosure is a flexible enclosure and wherein pressurizing includes increasing a gas pressure external to the flexible enclosure.

In a further example of the first aspect and the above examples, the method further includes repeating pressurizing and depressurizing, wherein the reagent is further mixed with the fluid.

In an additional example of the first aspect and the above examples, the fluid flows into the internal cavity of the container and compresses the compressible volume until the pressure within the internal cavity and exerted on the compressible volume is approximately equal to a pressure within the enclosure and external to the container.

In another example of the first aspect and the above examples, upon depressurizing, a pressure within the internal cavity as imposed by the compressible volume is greater than a pressure within the enclosure and external to the container, the fluid and the reagent eject from the internal cavity through the passage until the pressure within the internal cavity is approximately equal to a pressure within the enclosure and external to the container.

In a further example of the first aspect and the above examples, the method of releasing the fluid and the reagent through the fluid port.

In a second aspect, an apparatus includes an enclosure; a container disposed within the enclosure, the container defining an internal cavity having a compressible volume and defining a passage providing fluidic communication between the internal cavity and the exterior of the container; and a reagent disposed within the internal cavity.

In an example of the second aspect, the apparatus further includes a compressible member disposed within the internal cavity.

In another example of the second aspect and the above examples, the compressible member includes a resilient foam.

In a further example of the second aspect and the above examples, the enclosure is a flexible enclosure.

In an additional example of the second aspect and the above examples, the enclosure includes a fluid port to provide fluid access to the interior of the enclosure.

In another example of the second aspect and the above examples, the apparatus further includes an arm coupled to the container.

In a further example of the second aspect and the above examples, the apparatus further includes a set of arms coupled to the container to position the container approximately centrally within the enclosure.

In an additional example of the second aspect and the above examples, the apparatus further includes an arm coupled to the container and the fluid port to position the container approximately centrally within the enclosure.

In another example of the second aspect and the above examples, the container includes an insert coupled to a fitting to form the internal cavity.

In a further example of the second aspect and the above examples, the apparatus further includes a flange coupled to the container.

In an additional example of the second aspect and the above examples, the reagent comprises a lyophilized nucleotide or an analog thereof, a nucleotide solution, or a pH-adjusting solution.

In another example of the second aspect and the above examples, the apparatus further includes a cartridge defining a volume, the enclosure disposed within the volume.

In a further example of the second aspect and the above examples, the cartridge includes a gas inlet port providing access to the volume and external to the enclosure.

In an additional example of the second aspect and the above examples, the cartridge includes a lid to secure the enclosure and provide fluidic access to a fluid port of the enclosure.

In a third aspect, an apparatus includes a case defining a volume and having a gas port; and a plurality of enclosures disposed within the volume and secured to the case. Each enclosure of the plurality of enclosures includes a fluid port providing fluidic access to the interior of the enclosure; a container disposed within the each enclosure, the container defining an internal cavity having a compressible volume and defining a passage providing fluidic communication between the internal cavity and the exterior of the container; and a reagent disposed within the internal cavity.

In an example of the third aspect, the apparatus further includes a compressible member disposed within the internal cavity. For example, the compressible member includes a resilient foam.

In another example of the third aspect and the above examples, the each enclosure of the plurality of enclosures is secured to the container, the container providing fluidic access to the fluid port of the each enclosure.

In a further example of the third aspect and the above examples, the container is secured to the enclosure through an arm coupling the container to the enclosure.

In an additional example of the third aspect and the above examples, the enclosure is a bag enclosure.

In another example of the third aspect and the above examples, the each enclosure further includes a set of arms coupled to the container to position the container approximately centrally within the enclosure.

In a further example of the third aspect and the above examples, the reagent of the each enclosure includes a unique lyophilized nucleotide or an analog thereof, a nucleotide solution, or a pH-adjusting solution.

In an additional example of the third aspect and the above examples, the container includes an insert coupled to a fitting to form the internal cavity.

In another example of the third aspect and the above examples, the apparatus further includes a flange coupled to the container and the fluid port.

In a fourth aspect, a method for preparing a reagent solution includes filling an enclosure with a fluid through a fluid port of the enclosure. The enclosure includes a container disposed within the enclosure, the container defining an internal cavity having a compressible volume and defining a passage providing fluidic communication between the internal cavity and the exterior of the container; and a reagent disposed within the internal cavity. The method further includes pressurizing the fluid within the enclosure, the fluid flowing into the internal cavity of the container and compressing the compressible member; and depressurizing the fluid within the enclosure, the compressible member decompressing and ejecting the fluid and reagent from the internal cavity, the reagent mixing with the fluid.

In an example of the fourth aspect, the container further includes a compressible member disposed within the internal cavity.

In another example of the fourth aspect and the above examples, the enclosure is a flexible enclosure and wherein pressurizing includes increasing a gas pressure external to the flexible enclosure.

In a further example of the fourth aspect and the above examples, the enclosure is disposed within a case, wherein pressurizing includes increasing a gas pressure within the case and external to the enclosure.

In an additional example of the fourth aspect and the above examples, the method further includes repeating pressurizing and depressurizing, wherein the reagent is further mixed with the fluid.

In a further example of the fourth aspect and the above examples, the fluid flows into the internal cavity of the container and compresses the compressible member until the pressure within the internal cavity and exerted on the compressible member is approximately equal to a pressure within the enclosure and external to the container. In an additional example, wherein upon depressurizing, a pressure within the internal cavity as imposed by the compressible member is greater than a pressure within the enclosure and external to the container, the fluid and the reagent eject from the internal cavity through the passage until the pressure within the internal cavity is approximately equal to a pressure within the enclosure and external to the container.

In an additional example of the fourth aspect and the above examples, the method further includes releasing the fluid and the reagent through the fluid port.

In a fifth aspect, a method of preparing a reagent solution includes inserting a container into an enclosure, the container defining an internal cavity and defining a passage providing fluidic communication between the internal cavity and the exterior of the container. The container includes a compressible member disposed within the internal cavity and a reagent disposed within the internal cavity. The method also includes sealing the container within the enclosure with a fluid port; filling the enclosure with a fluid through the fluid port; pressurizing the fluid within the enclosure, the fluid flowing into the internal cavity of the container and compressing the compressible member; and depressurizing the fluid within the enclosure, the compressible member decompressing and ejecting the fluid and reagent from the internal cavity, the reagent mixing with the fluid.

In an example of the fifth aspect, the enclosure is a flexible enclosure and wherein pressurizing includes increasing a gas pressure external to the flexible enclosure.

In another example of the fifth aspect and the above examples, the enclosure is disposed within a case, wherein pressurizing includes increasing a gas pressure within the case and external to the enclosure.

In a further example of the fifth aspect and the above examples, the method further includes repeating pressurizing and depressurizing, wherein the reagent is further mixed with the fluid.

In an additional example of the fifth aspect and the above examples, the fluid flows into the internal cavity of the container and compresses the compressible member until the pressure within the internal cavity and exerted on the compressible member is approximately equal to a pressure within the enclosure and external to the container.

In another example of the fifth aspect and the above examples, wherein upon depressurizing, a pressure within the internal cavity as imposed by the compressible member is greater than a pressure within the enclosure and external to the container, the fluid and the reagent eject from the internal cavity through the passage until the pressure within the internal cavity is approximately equal to a pressure within the enclosure and external to the container.

In a further example of the fifth aspect and the above examples, the method further includes releasing the fluid and the reagent through the fluid port.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of preparing a reagent solution, the method comprising:
    providing a plurality of enclosures within a volume of a cartridge, the cartridge including a gas port, and an enclosure of the plurality of enclosures including:
        a container disposed within the enclosure, the container defining an internal cavity internal to the container and the container defining a passage providing fluidic communication between the internal cavity of the container and the exterior of the container interior to the enclosure; and
        a reagent disposed within the internal cavity;
    filling the enclosure with a fluid through a fluid port of the enclosure;
    increasing a gas pressure of the volume of the cartridge via the gas port to pressurize the fluid within the enclosure, the fluid flowing into the internal cavity of the container through the passage, contacting the reagent, and compressing a compressible volume within the internal cavity; and
    decreasing the gas pressure of the volume of the cartridge via the gas port to depressurize the fluid within the enclosure, the compressible volume decompressing and ejecting the fluid and the reagent from the internal cavity through the passage, the reagent mixing with the fluid within the enclosure.

2. The method of claim 1, further comprising a compressible member disposed within the internal cavity.

3. The method of claim 1, wherein the enclosure is a flexible enclosure and wherein pressurizing includes increasing a gas pressure external to the flexible enclosure.

4. The method of claim 1, further comprising repeating pressurizing and depressurizing, wherein the reagent is further mixed with the fluid.

5. The method of claim 1, wherein the fluid flows into the internal cavity of the container and compresses the compressible volume until the pressure within the internal cavity and exerted on the compressible volume is approximately equal to a pressure within the enclosure and external to the container.

6. The method of claim 1, wherein upon depressurizing, a pressure within the internal cavity as imposed by the compressible volume is greater than a pressure within the enclosure and external to the container, the fluid and the reagent ejecting from the internal cavity through the passage until the pressure within the internal cavity is approximately equal to a pressure within the enclosure and external to the container.

7. The method of claim 1, further comprising releasing the fluid and the reagent through the fluid port.

8. An apparatus comprising:
    a cartridge defining a volume, the cartridge including a gas inlet port providing access to the volume;
    an enclosure disposed and entirely enclosed within the volume and defining a space isolated from the volume, the enclosure being flexible to transfer pressure of the volume to fluids within the space of the enclosure;
    a container disposed and entirely enclosed within the enclosure, the container defining an internal cavity having a compressible volume and defining a passage providing fluidic communication between the internal cavity and the space of the enclosure exterior of the container; and a reagent disposed within the internal cavity.

9. The apparatus of claim 8, further comprising a compressible member disposed within the internal cavity.

10. The apparatus of claim 9, wherein the compressible member includes a resilient foam.

11. The apparatus of claim 8, wherein the enclosure includes a fluid port to provide fluid access to the interior of the enclosure.

12. The apparatus of claim 8, further comprising an arm coupled to the container.

13. The apparatus of claim 8, further comprising a set of arms coupled to the container to position the container approximately centrally within the enclosure.

14. The apparatus of claim 8, further comprising an arm coupled to the container and the fluid port to position the container approximately centrally within the enclosure.

15. The apparatus of claim 8, wherein the container includes an insert coupled to a fitting to form the internal cavity.

16. The apparatus of claim 8, further comprising a flange coupled to the container.

17. The apparatus of claim 8, wherein the reagent comprises a lyophilized nucleotide or an analog thereof, a nucleotide solution, or a pH-adjusting solution.

* * * * *